(12) United States Patent
Followell

(10) Patent No.: US 9,002,661 B2
(45) Date of Patent: Apr. 7, 2015

(54) AUTOMATED TIRE INSPECTIONS UTILIZING FLUORESCING NANO-PARTICLES

(75) Inventor: David A. Followell, Wildwood, MO (US)

(73) Assignee: The Boeing Company, Chicago, IL (US)

( * ) Notice: Subject to any disclaimer, the term of this patent is extended or adjusted under 35 U.S.C. 154(b) by 547 days.

(21) Appl. No.: 12/869,427

(22) Filed: Aug. 26, 2010

(65) Prior Publication Data

US 2012/0053876 A1    Mar. 1, 2012

(51) Int. Cl.
*G01T 1/10* (2006.01)
*G01N 21/84* (2006.01)
*B60C 11/24* (2006.01)

(52) U.S. Cl.
CPC ............ *G01N 21/8422* (2013.01); *B60C 11/24* (2013.01)

(58) Field of Classification Search
USPC ................ 702/34, 35, 57, 183, 188; 340/438; 152/151, 152.1
See application file for complete search history.

(56) References Cited

U.S. PATENT DOCUMENTS

| | | | |
|---|---|---|---|
| 2,301,251 A | 11/1942 | Capen | |
| 3,934,144 A | 1/1976 | Green et al. | |
| 4,032,785 A | 6/1977 | Green et al. | |
| 5,987,978 A | 11/1999 | Whitehead | |
| 7,353,700 B2 * | 4/2008 | Pullini et al. | 73/146 |
| 2004/0084120 A1* | 5/2004 | Arnold et al. | 152/151 |
| 2005/0061069 A1 | 3/2005 | Robert | |
| 2005/0242935 A1 | 11/2005 | Kafrawy | |
| 2007/0279827 A1 | 12/2007 | Sinnett et al. | |
| 2010/0094566 A1 | 4/2010 | Grant et al. | |

FOREIGN PATENT DOCUMENTS

| | | |
|---|---|---|
| DE | 19745734 A1 | 4/1999 |
| DE | 102008058882 A1 | 6/2010 |
| GB | 2243584 A | 3/1991 |
| GB | 2265586 A | 6/1993 |
| WO | 03076953 A2 | 9/2003 |
| WO | 2004050391 A1 | 6/2004 |
| WO | 2004068095 A1 | 8/2004 |
| WO | 2007002266 A2 | 1/2007 |

OTHER PUBLICATIONS

International Search Report and Written Opinion of PCT/US2011/030185 dated Jun. 29, 2011; 11 pages.
International Search Report and Written Opinion of PCT/US2011/030177 dated Jul. 1, 2011; 10 pages.

* cited by examiner

*Primary Examiner* — Mohamed Charioui
(74) *Attorney, Agent, or Firm* — Armstrong Teasdale LLP

(57) ABSTRACT

Methods and systems are provided for monitoring a structural health of an object. A state of fluorescence of at least one particle associated with the object is identified, and a structural health parameter associated with the object is determined based on the identified state of fluorescence of the at least one particle.

9 Claims, 4 Drawing Sheets

AUTOMATED TIRE INSPECTIONS UTILIZING FLUORESCING NANO-PARTICLES

BACKGROUND

The present disclosure relates generally to structural health monitoring and, more particularly, to inspecting an object utilizing fluorescing nano-particles.

Depending on the field and technology, known objects may be routinely inspected to determine whether any weaknesses and/or conditions that could adversely impact and/or limit the structural health of the object have developed. Such inspections may be completed using visually, mechanically, and/or chemically driven technologies. For example, aircraft tires are typically visually inspected by certified mechanics on a periodic basis to determine whether the tires are suitable for use. Such visual inspections are often time-consuming and, because of the subjectivity of the inspector, such inspections may be difficult to duplicate. As a result, visually inspecting each aircraft tire could create undesirable delays and/or expenses. Moreover, assigning a certified mechanic to each airport and/or aircraft may be cost-prohibitive.

BRIEF DESCRIPTION

In one aspect, a method is provided for monitoring a structural health of an object. The method includes identifying a state of fluorescence of at least one particle associated with the object and determining a structural health parameter associated with the object based on the identified state of fluorescence of the at least one particle.

In another aspect, a computing device is provided for determining a structural health of an object. The computing device is programmed to identify a state of fluorescence of at least one particle associated with the object, and determine a structural health parameter associated with the object based on the identified state of fluorescence of the at least one particle.

In yet another aspect, a system is provided for determining a structural health of an object. The system includes at least one particle associated with the object and a computing device. The computing device is programmed to identify a state of fluorescence of the at least one particle associated with the object, and determine a structural health parameter associated with the object based on the identified state of fluorescence of the at least one particle.

The features, functions, and advantages that have been discussed can be achieved independently in various embodiments of the present invention or may be combined in yet other embodiments further details of which can be seen with reference to the following description and drawings.

DETAILED DESCRIPTION

The subject matter described herein relates generally to structural health monitoring systems and more particularly to methods and systems for inspecting an object utilizing fluorescing nano-particles. In one embodiment, a tire is embedded with fluorescing nano-particles, which are exposed during the operating life of the tire. Such exposure, in combination with appropriate stimulation, will induce the nano-particles in to a state of fluorescence. As such, a color and/or at an intensity of the fluorescing nano-particles may be indicative of a structural health of the tire. Although the present disclosure is described in the context of inspecting a tire, it should be understood that the subject matter described herein may be used in other contexts in which it is desirable to monitor a structural health of an object.

Exemplary technical effects of the methods, systems, and computer-readable media described herein include at least one of: (a) stimulating at least one particle to emit a particle signal, (b) detecting the particle signal emitted by the at least one particle; (c) identifying a state of fluorescence of the at least one particle; (d) determining a structural health parameter associated with the object based on the identified state of fluorescence; and (e) comparing the structural health parameter to a predefined threshold.

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 1:
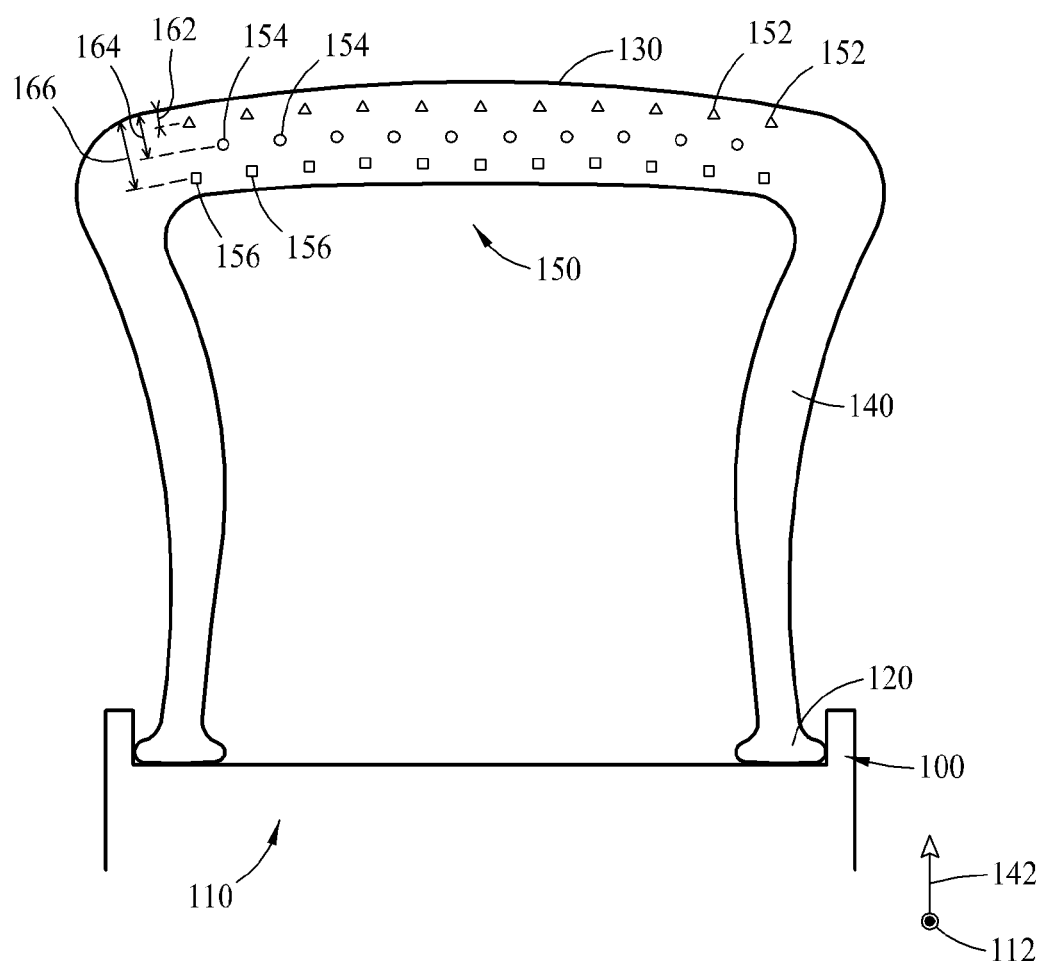
FIG. 1 is a cross-sectional view of an exemplary tire that may be inspected.

FIG. 1 is a cross-sectional view of an exemplary tire 100 that may be inspected. Alternatively, objects other than tire 100 may be monitored. In the exemplary embodiment, tire 100 has a toroidal body sized to fit about a wheel rim 110 along a circumferential axis 112 (substantially perpendicular to FIG. 1, shown in FIG. 2). In the exemplary embodiment, tire 100 includes a bead 120, a tread 130, and a sidewall 140 that extends between bead 120 and tread 130. Bead 120, tread 130, and sidewall 140 extend about wheel rim 110 along circumferential axis 112. In the exemplary embodiment, bead 120 and/or sidewall 140 facilitates supporting tread 130 along a radial axis 142, which enables tire 100 to generate traction against a surface (not shown).

In the exemplary embodiment, a plurality of particles 150 are coupled to tire 100. In the exemplary embodiment, particles 150 are nano-particles configured to fluoresce upon stimulation. In one embodiment, a structural health parameter of tire 100 may be determined based on a wavelength and/or an intensity of the fluorescence of particles 150. Moreover, in at least some embodiments, particles 150 may have a plurality of states of fluorescence. For example, in the exemplary embodiment, a plurality of first particles 152 are configured to emit a first particle signal, a plurality of second particles 154 are configured to emit a second particle signal, and a plurality of third particles 156 are configured to emit a third particle signal.

In the exemplary embodiment, particles 150 are substantially uniformly disposed about tire 100 along circumferential axis 112. In one embodiment, particles 150 may be embedded within tire 100 at varying depths of tread 130. For example, in the exemplary embodiment, first particles 152 are disposed at a first depth 162, second particles 154 are disposed at a second depth 164, and third particles 156 are disposed at a third depth 166. Moreover, in at least some embodiments, particles 152, 154, and/or 156 may be positioned in varying densities. As such, in the exemplary embodiment, as tire 100 is used and/or damaged and particles 152, 154, and/or 156 are exposed, a structural health parameter of tire 100 may be determined based on whether particles 152, 154, and/or 156 are stimulated to a state of fluorescence and/or a wavelength and/or an intensity of the fluorescence.

Figure 2:
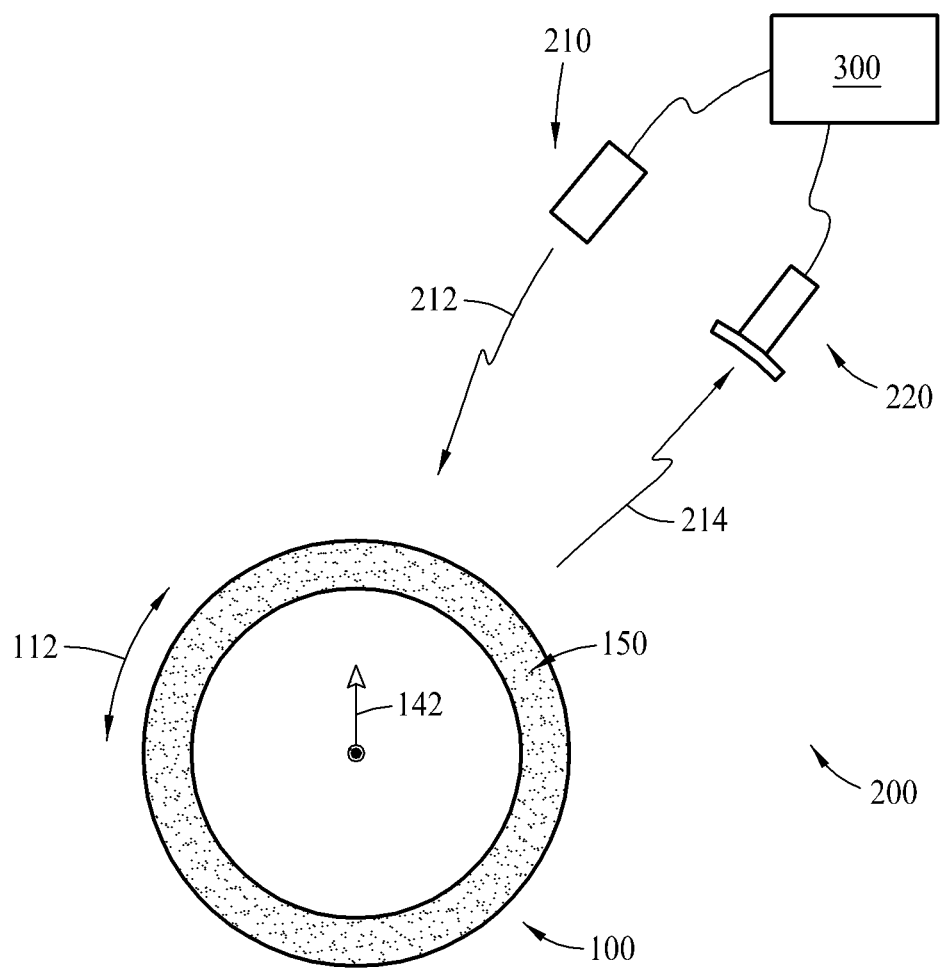
FIG. 2 is an exemplary system that may be used to monitor the structural health of the tire shown in FIG. 1.

FIG. 2 is an exemplary system 200 that may be used to monitor the structural health of an object, such as tire 100. In the exemplary embodiment, system 200 includes a stimulator 210 configured to stimulate at least one particle 150 into a state of fluorescence, a sensor 220 configured to detect a particle signal emitted by at least one particle 150, and a computing device 300.

In the exemplary embodiment, stimulator 210 transmits a signal 212 and/or emits a photon toward tire 100 and, more specifically, toward particles 150. In one embodiment, stimulator 210 is a laser and/or a light-emitting diode (LED). In the exemplary embodiment, stimulator 210 is communicatively coupled to computing device 300 such that communication signals may be transmitted between stimulator 210 and computing device 300.

In the exemplary embodiment, sensor 220 receives a signal 214 and/or detects a photon emitted by a stimulated particle 150. For example, in one embodiment, a stimulated particle 150 may emit a photon 214 having a wavelength between approximately 390 nm and approximately 750 nm. In such an embodiment, photon 214 may be visible to the naked eye. Alternatively, in another embodiment, the stimulated particle 150 may emit a photon 214 having a wavelength less than or equal to approximately 390 nm and/or greater than or equal to approximately 750 nm. In such an embodiment, photon 214 may be detectable using a suitable sensor 220. In the exemplary embodiment, sensor 220 is communicatively coupled to computing device 300 such that communication signals may be transmitted between sensor 220 and computing device 300.

Figure 3:
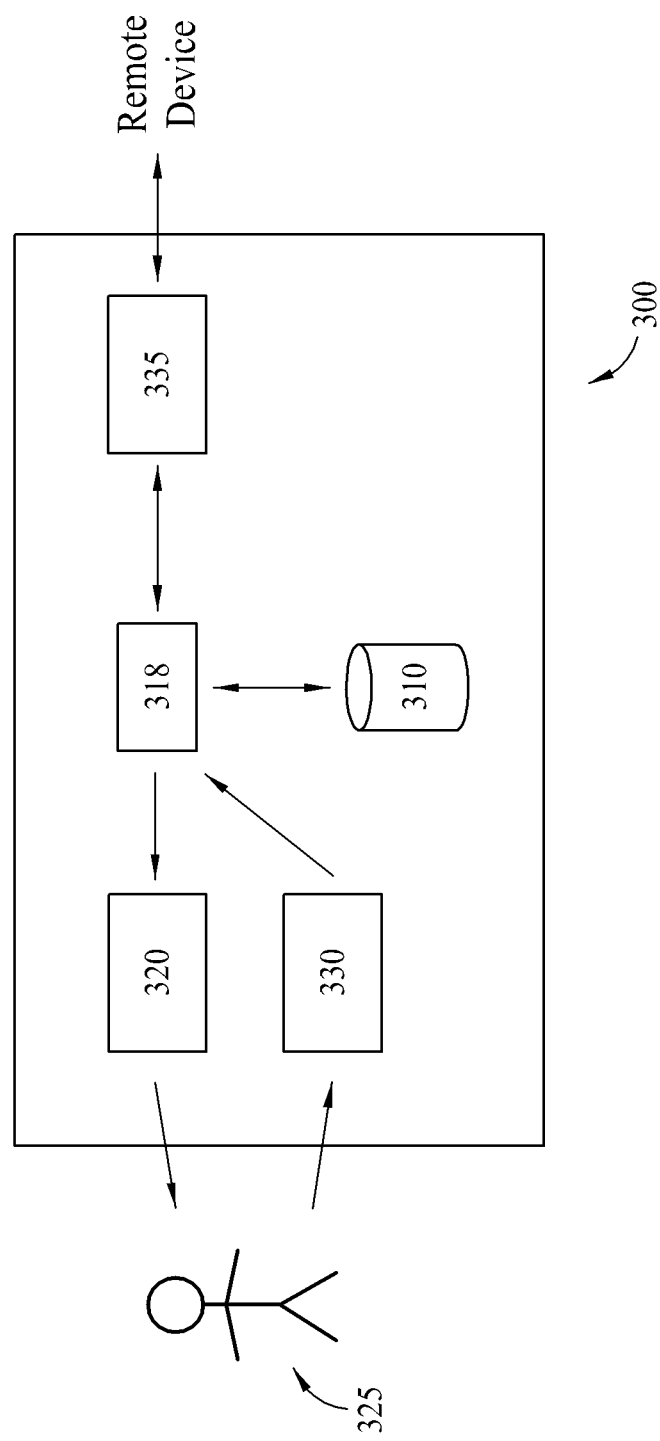
FIG. 3 is block diagram of an exemplary computing device that may be used with the system shown in FIG. 2.

FIG. 3 is block diagram of computing device 300 including a memory device 310 and a processor 318 coupled to memory device 310 for executing programmed instructions. Processor 318 may include one or more processing units (e.g., in a multi-core configuration). In one embodiment, executable instructions and/or structural health data are stored in memory device 310. For example, in the exemplary embodiment, memory device 310 stores software for use in interpreting the wavelength and/or the intensity of the fluorescence of particles 150 to determine a structural health parameter of tire 100. Computing device 300 is programmable to perform one or more operations described herein by programming memory device 310 and/or processor 318. For example, processor 318 may be programmed by encoding an operation as one or more executable instructions and providing the executable instructions in memory device 310.

Processor 318 may include, but is not limited to, a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

Memory device 310, as described herein, is one or more devices that enable information such as executable instructions and/or other data to be stored and retrieved. Memory device 310 may include one or more computer readable media, such as, without limitation, dynamic random access memory (DRAM), static random access memory (SRAM), a solid state disk, and/or a hard disk. Memory device 310 may be configured to store, without limitation, executable instructions, structural health data, and/or any other type of data suitable for use with the methods and systems described herein.

In the exemplary embodiment, computing device 300 includes a presentation interface 320 that is coupled to processor 318. Presentation interface 320 outputs (e.g., display, print, and/or otherwise output) information, such as, but not limited to, configuration data, structural health data and/or any other type of data to a user 325. For example, presentation interface 320 may include a display adapter (not shown in FIG. 1) that is coupled to a display device, such as a cathode ray tube (CRT), a liquid crystal display (LCD), a light-emitting diode (LED) display, an organic LED (OLED) display, and/or an "electronic ink" display. In some embodiments, presentation interface 320 includes more than one display device. In addition, or in the alternative, presentation interface 320 may include a printer.

In the exemplary embodiment, computing device 300 includes an input interface 330 that receives input from user 325. For example, input interface 330 may be configured to receive an indication of structural health data and/or any other type of data suitable for use with the methods and systems described herein. As described in further detail below, computing device 300 uses the received input to monitor a structural health of tire 100. In the exemplary embodiment, input interface 330 is coupled to processor 318 and may include, for example, a keyboard, a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 320 and as input interface 330.

In the exemplary embodiment, computing device 300 includes a communication interface 335 coupled to memory device 310 and/or processor 318. Communication interface 335 is coupled in communication with a remote device, such as stimulator 210, sensor 220, and/or another computing device 300. For example, communication interface 335 may include, without limitation, a wired network adapter, a wireless network adapter, and/or a mobile telecommunications adapter.

Figure 4:
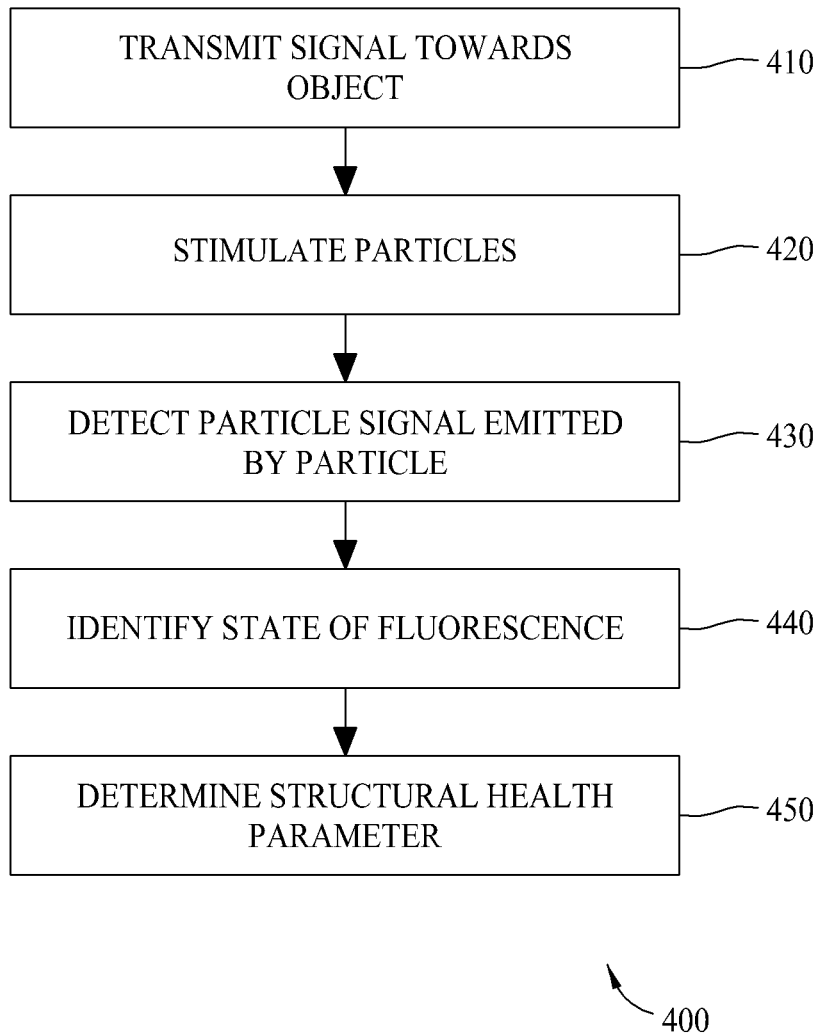
FIG. 4 is a flow chart illustrating an exemplary method for monitoring a structural health of the tire shown in FIG. 1 using the system shown in FIG. 2.

FIG. 4 is a flow chart illustrating an exemplary method 400 for use in monitoring a structural health of tire 100. Initially, in the exemplary embodiment, computing device 300 is programmed to direct stimulator 210 to transmit 410 a signal 212 toward tire 100. In the exemplary embodiment, at least some particles 150 embedded within tire 100, namely the exposed particles 150, are stimulated 420 by transmission 410 to a state of fluorescence. Particularly, in the exemplary embodiment, the stimulated particles 150 fluoresce to emit a particle signal 214 having a wavelength and/or an intensity. More particularly, in the exemplary embodiment, particles 152, 154, and/or 156 are stimulated 420 to emit a respective particle signal 214.

In the exemplary embodiment, sensor 220 detects 430 a particle signal 214 emitted by at least one stimulated particle 150. In the exemplary embodiment, sensor 220 generates a sensor signal representative of the detected particle signal, particularly the signal's wavelength and intensity, and transmits the sensor signal to computing device 300. In the exemplary embodiment, computing device 300 is programmed to identify 440 a state of fluorescence for particle 150 based on the transmitted sensor signal and, thus, the detected particle signal 214. As such, in the exemplary embodiment, computing device 300 is programmed to determine the health of tire 100 based at least on the wavelength and/or an intensity of the fluorescence of particles 150. In one embodiment, computing device 300 may determine whether particles 152, 154, and/or 156 have emitted a particle signal.

In the exemplary embodiment, computing device 300 is programmed to determine 450 a structural health parameter for tire 100 based on the identified state of fluorescence. The structural health parameter may include an object status, a remaining useful life, and/or a presence of an anomaly. For example, in one embodiment, computing device 300 may determine that tire 100 is in "PASS" status and/or has a long remaining useful life if particles 152 are fluorescing, tire 100 is in "WARNING" status and/or has a medium remaining useful life if particles 154 are fluorescing, and tire 100 is in "REPLACE" status and/or has a short remaining useful life if particles 156 are fluorescing. In one embodiment, the structural health parameter may be compared to at least one predefined threshold for the structural health parameter to enable the object status, the remaining useful life, and/or the presence of an anomaly to be determined. Moreover, in at least some embodiments, the structural health parameter may be automatically updated and/or stored within memory device 310.

The above-described systems and methods facilitate automatically inspecting an object to determine whether any weakness and/or condition that could potentially impact the structural health of the object has developed. As such, the embodiments described herein facilitate inspecting the object in remote locations and/or increasing an amount of time between manual inspections. Accordingly, the embodiments described herein enable increased flexibility and/or reduced costs.

The exemplary systems and methods are not limited to the specific embodiments described herein, but rather, components of each system and/or steps of each method may be utilized independently and separately from other components and/or method steps described herein. Each component and each method step may also be used in combination with other components and/or method steps.

This written description uses examples to disclose certain embodiments of the invention, including the best mode, and also to enable any person skilled in the art to practice those certain embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for monitoring a structural health of an object, said method comprising:
    directing a signal towards the object that includes a first particle originally at a first depth within the object and a second particle originally at a second deeper depth within the object, wherein at least one of the first particle and the second particle may be exposed at a surface of the object, wherein the signal is configured to stimulate at least one of the first particle and the second particle to a state of fluorescence, wherein the first particle is configured to emit a first particle signal and the second particle is configured to emit a second particle signal that is different than the first particle signal;
    receiving at least one of the first particle signal and the second particle signal as a result of stimulating the at least one of the first particle and the second particle, wherein the stimulation is based on which of the first and second particles are exposed at the surface of the object;
    identifying the state of fluorescence of the at least one of the first particle signal and the second particle signal associated with the object based on the received at least one of the first particle signal and the second particle signal;
    determining a first structural health parameter associated with the object based on whether only the first particle signal is received and identified; and
    determining a second structural health parameter associated with the object based on whether the second particle signal is received and identified.

2. A method in accordance with claim 1 further comprising comparing at least one of the first and second structural health parameters to a predefined threshold.

3. A computing device for use in determining a structural health of an object, said computing device programmed to:
    direct a signal towards the object that includes a first particle originally at a first depth within the object and a second particle originally at a second deeper depth within the object, wherein at least one of the first particle and the second particle may be exposed at a surface of the object, wherein the signal is configured to stimulate at least one of the first particle and the second particle to a state of fluorescence, wherein the first particle is configured to emit a first particle signal and the second particle is configured to emit a second particle signal that is different than the first particle signal;
    receive at least one of the first particle signal and the second particle signal as a result of stimulating the at least one of the first particle and the second particle, wherein the stimulation is based on which of the first and second particles are exposed at the surface of the object;
    identify the state of fluorescence of the at least one of the first particle signal and the second particle signal associated with the object based on the received at least one of the first particle signal and the second particle signal;
    determine a first structural health parameter associated with the object based on whether only the first particle signal is received and identified; and
    determine a second structural health parameter associated with the object based on whether the second particle signal is received and identified.

4. A computing device in accordance with claim 3 communicatively coupled to a sensor, said computing device further programmed to receive a sensor signal representative of the one of the first particle signal and the second particle signal emitted by the first and second particles.

5. A computing device in accordance with claim 3 further programmed to compare at least one of the first and second structural health parameters to a predefined threshold.

6. A system for use in determining a structural health of an object, said system comprising:
    a first particle originally at a first depth within the object and a second particle originally at a second deeper depth within the object, wherein the first and second particles may be exposed at a surface of the object;
    a stimulator configured to direct a signal towards the object such that at least one of the first particle and the second particle is stimulated to a state of fluorescence;

a sensor configured to detect a particle signal emitted by at least one of the first particle and the second particle; and a computing device programmed to:

instruct the stimulator to direct the signal towards the object, wherein the first particle is configured to emit a first particle signal and the second particle is configured to emit a second particle signal that is different than the first particle signal;

receive, from the sensor, at least one of the first particle signal and the second particle signal as a result of stimulating the at least one of the first particle and the second particle, wherein the stimulation is based on which of the first and second particles are exposed at the surface of the object;

identify the state of fluorescence of the at least one of the first particle signal and the second particle signal associated with the object based on the received at least one of the first particle signal and the second particle signal;

determine a first structural health parameter associated with the object based on whether only the first particle signal is received and identified; and determine a second structural health parameter associated with the object based on whether the second particle signal is received and identified.

7. A system in accordance with claim 6, wherein said computing device is further programmed to compare at least one of the first and second structural health parameters to a predefined threshold.

8. A method for monitoring a structural health of a tire, said method comprising:

directing a signal towards the tire that includes a first particle originally at a first depth within the tire and a second particle originally at a second deeper depth within the tire, wherein at least one of the first particle and the second particle may be exposed at a surface of the tire, wherein the signal is configured to stimulate at least one of the first particle and the second particle to a state of fluorescence, wherein the first particle is configured to emit a first particle signal and the second particle is configured to emit a second particle signal that is different than the first particle signal;

receiving at least one of the first particle signal and the second particle signal as a result of stimulating the at least one of the first particle and the second particle, wherein the stimulation is based on which of the first and second particles are exposed at the surface of the tire;

identifying the state of fluorescence of the at least one of the first particle signal and the second particle signal associated with the tire based on the received at least one of the first particle signal and the second particle signal;

determining a first structural health parameter associated with the tire based on whether only the first particle signal is received and identified; and determining a second structural health parameter associated with the tire based on whether the second particle signal is received and identified.

9. A method in accordance with claim 8 further comprising comparing at least one of the first and second structural health parameters to a predefined threshold.

* * * * *